United States Patent
Hagberg

(10) Patent No.: US 9,027,166 B1
(45) Date of Patent: May 12, 2015

(54) THERAPEUTIC SOCK SYSTEM AND METHOD

(76) Inventor: Jody Lynn Hagberg, Lawrenceville, GA (US)

( * ) Notice: Subject to any disclaimer, the term of this patent is extended or adjusted under 35 U.S.C. 154(b) by 661 days.

(21) Appl. No.: 13/199,899

(22) Filed: Sep. 12, 2011

Related U.S. Application Data

(63) Continuation-in-part of application No. 11/891,915, filed on Aug. 14, 2007, now abandoned.

(51) Int. Cl.
*A41B 11/00* (2006.01)

(52) U.S. Cl.
CPC ............. *A41B 11/00* (2013.01); *A41B 2400/32* (2013.01)

(58) Field of Classification Search
CPC .... A41B 11/00; A41B 11/004; A41B 11/005; A41B 11/10; A41B 11/121; A41B 11/126; A41B 2400/32
USPC ............ 2/239, 240, 241, 409; 66/178 R, 185; 602/62, 63
See application file for complete search history.

(56) References Cited

U.S. PATENT DOCUMENTS

| | | | | |
|---|---|---|---|---|
| 3,384,083 A | * | 5/1968 | Cozza et al. | 604/292 |
| 4,069,600 A | * | 1/1978 | Wise | 36/10 |
| 4,567,065 A | * | 1/1986 | Schneiderman | 427/230 |
| 5,325,541 A | * | 7/1994 | Willard | 2/239 |
| 5,402,540 A | * | 4/1995 | Williams | 2/239 |
| 5,483,703 A | * | 1/1996 | Williams | 2/239 |
| 5,592,690 A | * | 1/1997 | Wu | 2/67 |
| 5,614,202 A | * | 3/1997 | DeFina | 424/402 |
| 5,634,216 A | * | 6/1997 | Wu | 2/239 |
| 5,682,617 A | * | 11/1997 | Tumas | 2/239 |
| 5,697,106 A | * | 12/1997 | Baker et al. | 2/239 |
| 5,761,746 A | * | 6/1998 | Brown | 2/243.1 |
| 5,926,888 A | * | 7/1999 | Chen et al. | 12/142 EV |
| 6,041,443 A | * | 3/2000 | Pas et al. | 2/239 |
| 6,092,397 A | * | 7/2000 | Cortinovis | 66/184 |
| 6,117,119 A | * | 9/2000 | Gould | 604/290 |
| 6,153,139 A | * | 11/2000 | Marquette | 264/219 |
| 6,571,397 B1 | * | 6/2003 | Williams | 2/239 |
| 6,651,257 B2 | * | 11/2003 | Smith | 2/239 |
| 6,662,377 B2 | * | 12/2003 | Williams | 2/239 |
| 6,665,883 B2 | * | 12/2003 | Sloan | 2/239 |
| 6,673,054 B1 | * | 1/2004 | Gould et al. | 604/292 |
| 6,905,487 B2 | * | 6/2005 | Zimmerman | 604/292 |
| 6,931,767 B2 | * | 8/2005 | Royle | 36/111 |
| 6,953,582 B2 | * | 10/2005 | Chou | 424/402 |
| 2003/0126759 A1 | * | 7/2003 | Ross | 36/9 R |
| 2003/0131397 A1 | * | 7/2003 | Sloan | 2/239 |
| 2003/0145491 A1 | * | 8/2003 | Udugama | 36/23 |
| 2003/0154625 A1 | * | 8/2003 | Royle | 36/7.3 |
| 2003/0177566 A1 | * | 9/2003 | Williams | 2/239 |
| 2004/0078871 A1 | * | 4/2004 | Entwistle et al. | 2/239 |

(Continued)

*Primary Examiner* — Alissa L Hoey

(57) ABSTRACT

An interior sock is fabricated of a flexible elastic polymer. The interior sock has a cylindrical closed toe section, a cylindrical open ankle section and an intermediate heel section. The heel section is provided between the toe and ankle sections. An exterior sock is fabricated of a knitted blend of cotton and a minor portion of an elastic. The exterior sock has a cylindrical closed toe section, a cylindrical open ankle section and an intermediate heel section. The heel section is provided between the toe and ankle sections. A quantity of therapeutic fluid is located within the interior sock. The therapeutic fluid is in contact with a foot of a user. The interior sock provides support for the therapeutic fluid. The exterior sock provides pressure and warmth to the interior sock and the therapeutic fluid.

1 Claim, 4 Drawing Sheets

(56) References Cited

U.S. PATENT DOCUMENTS

| | | | |
|---|---|---|---|
| 2005/0246821 A1* | 11/2005 | Kopp et al. | 2/239 |
| 2006/0021112 A1* | 2/2006 | Roser et al. | 2/239 |
| 2006/0130216 A1* | 6/2006 | Allsebrook | 2/239 |
| 2006/0143802 A1* | 7/2006 | Butz | 2/239 |
| 2006/0179547 A1* | 8/2006 | Rosental-Reis et al. | 2/239 |
| 2006/0212997 A1* | 9/2006 | Blanchard | 2/239 |
| 2006/0260024 A1* | 11/2006 | Lee | 2/239 |
| 2009/0172867 A1* | 7/2009 | Kopp et al. | 2/239 |
| 2009/0211585 A1* | 8/2009 | Cumbie et al. | 128/849 |
| 2009/0241244 A1* | 10/2009 | Butz | 2/239 |

* cited by examiner

THERAPEUTIC SOCK SYSTEM AND METHOD

RELATED APPLICATION

The present application is a continuation-in-part of pending U.S. patent application Ser. No. 11/891,915 filed Aug. 14, 2007, now abandoned the subject matter of which is incorporated herein by reference.

BACKGROUND OF THE INVENTION

1. Field of the Invention

The present invention relates to a therapeutic sock system and method and more particularly pertains to increasing the effectiveness of foot medications, creams, lotions and ointments in a safe, efficient and cost effective manner.

2. Description of the Prior Art

The use of therapeutic systems and methods of known designs and configurations is known in the prior art. More specifically, therapeutic systems and methods of known designs and configurations previously devised and utilized for the purpose of covering feet through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Publication Number 2004/0078871 issued Apr. 29, 2004 to Entwistle et al. relating to a Foot and Leg Warmer. U.S. Pat. No. 6,665,883 issued Dec. 23, 2003 to Sloan relating to an Oversock. Lastly, U.S. Pat. No. 5,682,619 issued Nov. 4, 1997 to Tumas relating to a Latex Stocking Bandage.

While these devices fulfill their respective, particular objectives and requirements, the aforementioned patents do not describe a therapeutic system and method that allows for increasing the effectiveness of foot medications, creams, lotions and ointments in a safe, efficient and cost effective manner.

In this respect, the therapeutic sock system and method according to the present invention substantially departs from the conventional concepts and designs of the prior art, and in doing so provides an apparatus primarily developed for the purpose of increasing the effectiveness of foot medications, creams, lotions and ointments in a safe, efficient and cost effective manner.

Therefore, it can be appreciated that there exists a continuing need for a new and improved therapeutic sock system and method which can be used for increasing the effectiveness of foot medications, creams, lotions and ointments in a safe, efficient and cost effective manner. In this regard, the present invention, including the primary embodiment and the alternate embodiments of the invention, substantially fulfills this need.

SUMMARY OF THE INVENTION

In view of the foregoing disadvantages inherent in the known types of therapeutic systems and methods of known designs and configurations now present in the prior art, the present invention provides an improved therapeutic sock system and method. As such, the general purpose of the present invention, which will be described subsequently in greater detail, is to provide a new and improved therapeutic sock system and method and which has all the advantages of the prior art and none of the disadvantages.

To attain this, the present invention essentially comprises a therapeutic sock system and method. First provided is an interior sock. The interior sock is fabricated of a flexible elastic polymer. The flexible elastic polymer is selected from the class of flexible elastic polymers. The class of flexible elastic polymers includes latex and vinyl. The interior sock has a cylindrical closed toe section. The interior sock has a cylindrical open ankle section. The interior sock has an intermediate heel section. The intermediate heel section is provided between the toe and ankle sections. The toe and ankle sections have axes. The axes diverge at about 120 degrees from the heel section. The interior sock has a thickness of between 0.9 mils and 1.6 mils. The length of the foot portion of the interior sock is about 8 inches plus or minus 20 when measured along its axis. The length of the ankle portion of the interior sock is about 3 inches plus or minus 20 when measured along its axis.

An exterior sock is provided. The exterior sock is fabricated of a ribbed knitted blend. The knitted blend is at least 80 percent cotton and a minor portion of an elastic polymer. The exterior sock has a cylindrical closed toe section. The exterior sock has a cylindrical open ankle section. The exterior sock has an intermediate heel section. The intermediate heel section is provided between the toe and ankle sections. The toe and ankle sections have axes. The axes diverge at about 120 degrees from the heel section. The interior sock includes textured areas around the ankle portion. In this manner increased gripping capabilities are provided. The ankle section has a common thickness throughout the majority of its extent. The length of the foot portion of the interior sock is about 8 inches plus or minus 20 percent when measured along its axis. The length of the ankle portion of the interior sock is about 2 inches plus or minus 20 percent when measured along its axis.

Provided last is a quantity of therapeutic fluid. The therapeutic fluid is selected from the class of therapeutic fluids. The class of therapeutic fluids includes foot medications, creams, lotions and ointments. The therapeutic fluid is located within the interior sock. The therapeutic fluid is in contact with a foot of a user. The interior sock provides support for the therapeutic fluid. The exterior sock provides pressure and warmth to the interior sock and the therapeutic fluid.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved therapeutic sock system and method which has all of the advantages of the prior art therapeutic systems and methods of known designs and configurations and none of the disadvantages.

It is another object of the present invention to provide a new and improved therapeutic sock system and method which may be easily and efficiently manufactured and marketed.

It is further object of the present invention to provide a new and improved therapeutic sock system and method which is of durable and reliable constructions.

An even further object of the present invention is to provide a new and improved therapeutic sock system and method which is susceptible of a low cost of manufacture with regard to both materials and labor, and which accordingly is then susceptible of low prices of sale to the consuming public, thereby making such therapeutic sock system and method economically available to the buying public.

Even still another object of the present invention is to provide a therapeutic sock system and method for increasing the effectiveness of foot medications, creams, lotions and ointments in a safe, efficient and cost effective manner.

Lastly, it is an object of the present invention to provide a new and improved therapeutic sock system and method. An interior sock is fabricated of a flexible elastic polymer. The interior sock has a cylindrical closed toe section, a cylindrical open ankle section and an intermediate heel section. The heel section is provided between the toe and ankle sections. An exterior sock is fabricated of a knitted blend of cotton and a minor portion of an elastic. The exterior sock has a cylindrical closed toe section, a cylindrical open ankle section and an intermediate heel section. The heel section is provided between the toe and ankle sections. A quantity of therapeutic fluid is located within the interior sock. The therapeutic fluid is in contact with a foot of a user. The interior sock provides support for the therapeutic fluid. The exterior sock provides pressure and warmth to the interior sock and the therapeutic fluid.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
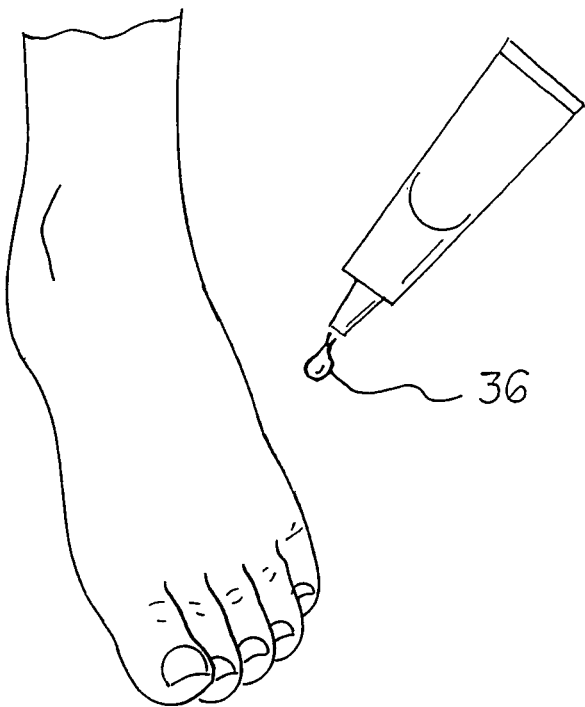
FIG. 1 is a perspective view of a foot with a therapeutic fluid being applied.
Figure 2:
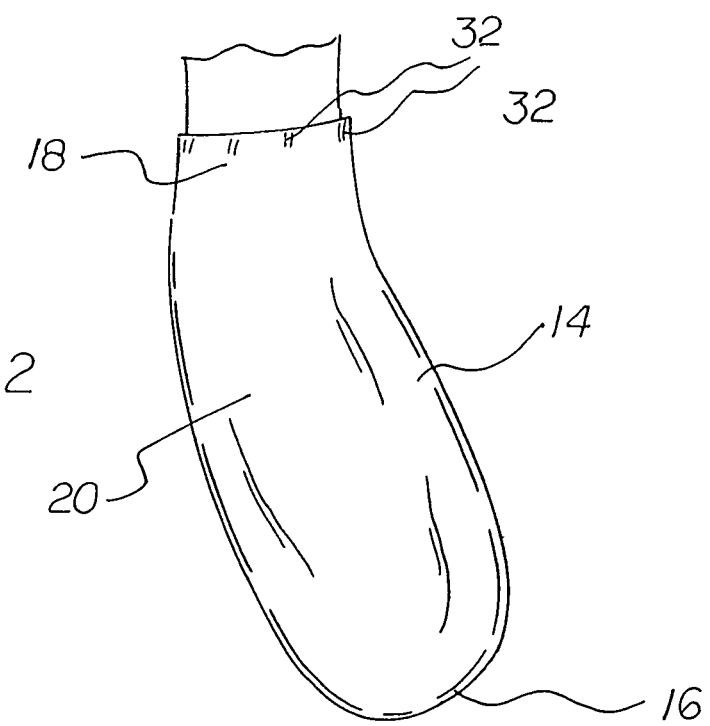
FIG. 2 is a perspective view of a foot covered by an interior sock fabricated of a flexible elastic polymer.
Figure 3:
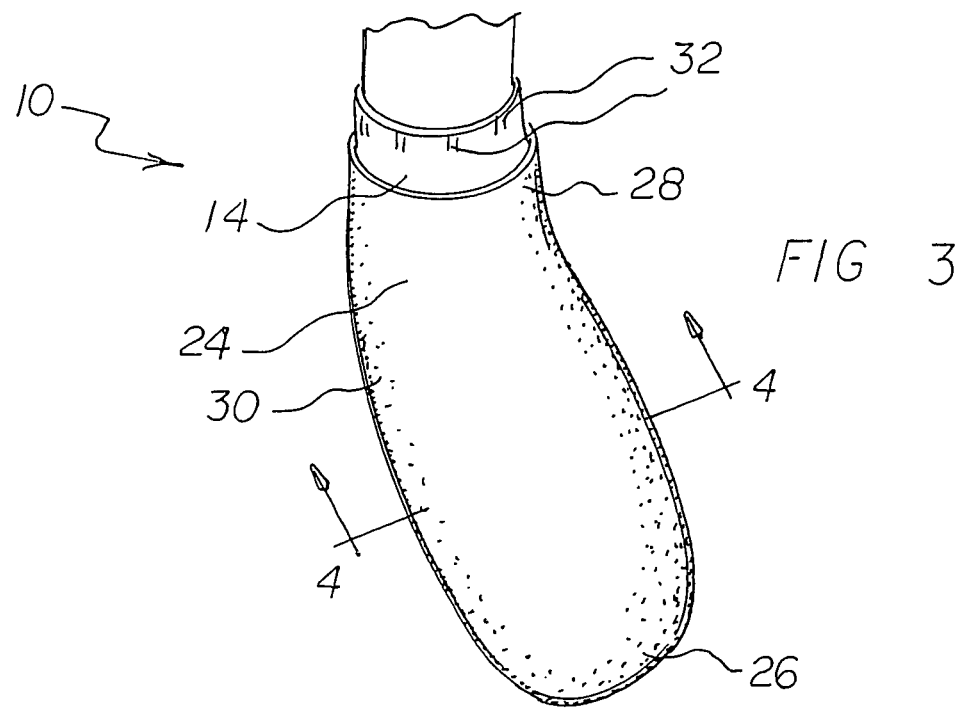
FIG. 3 is a perspective view of a therapeutic sock system constructed in accordance with the principles of the present invention.
Figure 4:
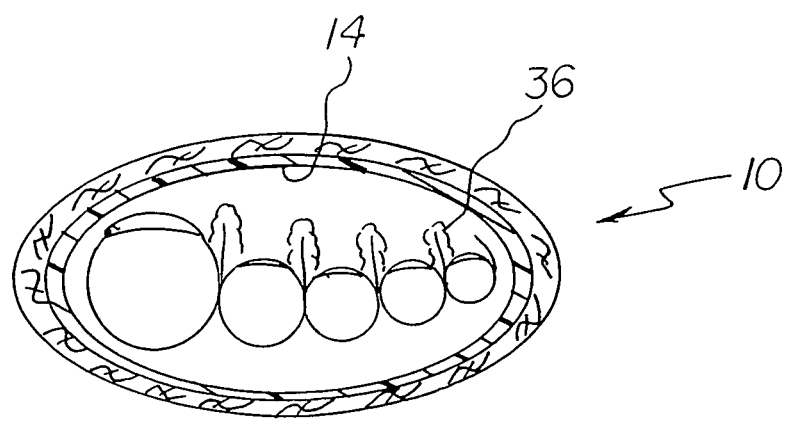
FIG. 4 is a cross sectional view taken along line 4-4 of FIG. 3.
Figure 5:
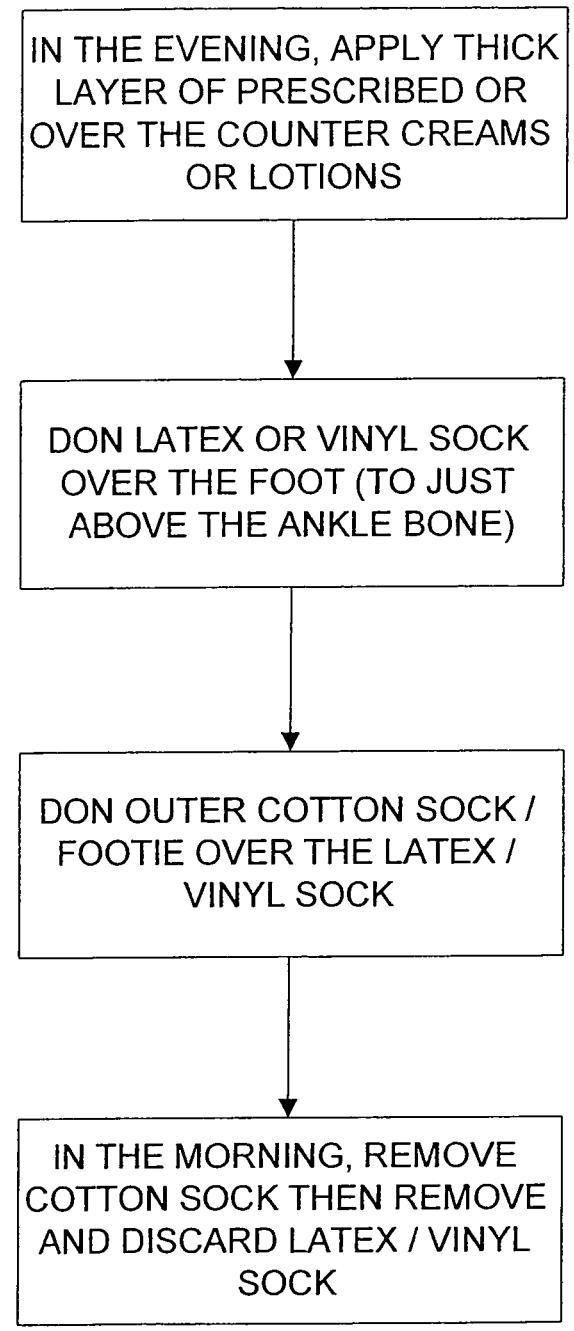
FIG. 5 is a flow diagram illustrating a therapeutic sock method practiced in accordance with the principles of the present invention.

With reference now to the drawings, and in particular to FIG. 1 thereof, the preferred embodiment of the new and improved therapeutic sock system and method embodying the principles and concepts of the present invention and generally designated by the reference numeral 10 will be described.

The present invention, the therapeutic sock system and method 10 is comprised of a plurality of components. Such components in their broadest context include an interior sock, an exterior sock and therapeutic fluid. Such components are individually configured and correlated with respect to each other so as to attain the desired objective.

First provided is an interior sock 14. The interior sock is fabricated of a flexible elastic polymer. The flexible elastic polymer is selected from the class of flexible elastic polymers. The class of flexible elastic polymers includes latex and vinyl. The interior sock has a cylindrical closed toe section 16. The interior sock has a cylindrical open ankle section 18. The interior sock has an intermediate heel section 20. The intermediate heel section is provided between the toe and ankle sections. The toe and ankle sections have axes. The axes diverge at about 120 degrees from the heel section. The interior sock has a thickness of between 0.9 mils and 1.6 mils.

The length of the foot portion of the interior sock is about 8 inches plus or minus 20 when measured along its axis. The length of the ankle portion of the interior sock is about 3 inches plus or minus 20 when measured along its axis.

The interior sock is adapted to be fabricated in any of a plurality of colors including clear and white and any other color. Such interior socks are intended to be available for men and women and children, in all sizes from extra small to extra large.

An exterior sock 24 is provided. The exterior sock is fabricated of a ribbed knitted blend. The knitted blend is at least 80 percent cotton and a minor portion of an elastic polymer. The exterior sock has a cylindrical closed toe section 26. The exterior sock has a cylindrical open ankle section 28. The exterior sock has an intermediate heel section 30. The intermediate heel section is provided between the toe and ankle sections. The toe and ankle sections have axes. The axes diverge at about 120 degrees from the heel section. The interior sock includes textured areas 32 around the ankle portion forming a beaded cuff. In this manner increased gripping capabilities are provided to facilitate donning. The ankle section has a common thickness throughout the majority of its extent. The length of the foot portion of the interior sock is about 8 inches plus or minus 20 percent when measured along its axis. The length of the ankle portion of the interior sock is about 2 inches plus or minus 20 percent when measured along its axis.

Provided last is a quantity of therapeutic fluid 36. The therapeutic fluid is selected from the class of therapeutic fluids. The class of therapeutic fluids includes foot medications, creams, lotions and ointments. The therapeutic fluid is located within the interior sock. The therapeutic fluid is in contact with a foot of a user. The interior sock provides support for the therapeutic fluid. The exterior sock provides pressure and warmth to the interior sock and the therapeutic fluid.

Although the therapeutic fluids function in a beneficial manner when used with a thin interior sock and a warmth promoting exterior sock, it has been surprisingly found that the therapeutic fluids function in an optimum manner when used with a thin interior sock, between 0.9 mils and 1.6 mils and with an exterior sock to provide warmth to promote the healing function of the therapeutic fluids.

In addition to the system as described above, the present invention also includes a therapeutic sock method as described and claimed herein.

The first step is providing an interior sock. The interior sock is fabricated of a flexible elastic polymer. The flexible elastic polymer is selected from the class of flexible elastic polymers. The class of flexible elastic polymers includes latex and vinyl. The interior sock has a cylindrical closed toe section. The interior sock has a cylindrical open ankle section. The interior sock has an intermediate heel section. The intermediate heel section is provided between the toe and ankle sections. The toe and ankle sections have axes. The axes diverge at about 120 degrees from the heel section. The interior sock has a thickness of between 0.9 mils and 1.6 mils. The length of the foot portion of the interior sock is about 8 inches plus or minus 20 when measured along its axis. The length of the ankle portion of the interior sock is about 3 inches plus or minus 20 when measured along its axis.

The second step is providing an exterior sock. The exterior sock is fabricated of a ribbed knitted blend. The knitted blend is at least 80 percent cotton and a minor portion of an elastic polymer. The exterior sock has a cylindrical closed toe section. The exterior sock has a cylindrical open ankle section. The exterior sock has an intermediate heel section. The intermediate heel section is provided between the toe and ankle sections. The toe and ankle sections have axes. The axes diverge at about 120 degrees from the heel section. The interior sock includes textured areas around the ankle portion. In this manner increased gripping capabilities are provided. The ankle section has a common thickness throughout the majority of its extent. The length of the foot portion of the interior sock is about 8 inches plus or minus 20 percent when measured along its axis. The length of the ankle portion of the interior sock is about 2 inches plus or minus 20 percent when measured along its axis.

The third step is providing a quantity of therapeutic fluid. The therapeutic fluid is selected from the class of therapeutic fluids. The class of therapeutic fluids includes foot medications, creams, lotions and ointments. The therapeutic fluid is located within the interior sock due to the application of the therapeutic fluid directly to the foot of the patient prior to the donning of the interior sock. The therapeutic fluid is in contact with a foot of a user. The interior sock provides support for the therapeutic fluid. The exterior sock provides pressure and warmth to the interior sock and the therapeutic fluid.

The fourth step is applying a thick layer of the therapeutic fluid to the foot in the evening. The therapeutic fluid is selected from the class of therapeutic fluids. The class of therapeutic fluids includes foot medications, creams, lotions and ointments.

The fifth step is donning the interior sock over the foot to just above the ankle bone. The interior sock is fabricated of a flexible elastic polymer. The flexible elastic polymer is selected from the class of flexible elastic polymers. The class of flexible elastic polymers includes latex and vinyl.

The sixth step is donning the exterior sock over the interior sock and fluid for retention purposes. The exterior sock is fabricated of a ribbed knitted blend. The knitted blend is at least 80 percent cotton and a minor portion of an elastic polymer.

The final step is removing the exterior sock in the morning then removing and discarding the interior sock.

The present invention serves the purpose of making medicated and over the counter fluids, creams, lotions and ointments more effective by occluding foot with cream on it, retaining the cream and making the foot sweat. As a result, deeper penetration of the fluids due to the sweating heals the foot faster.

Figure 6:
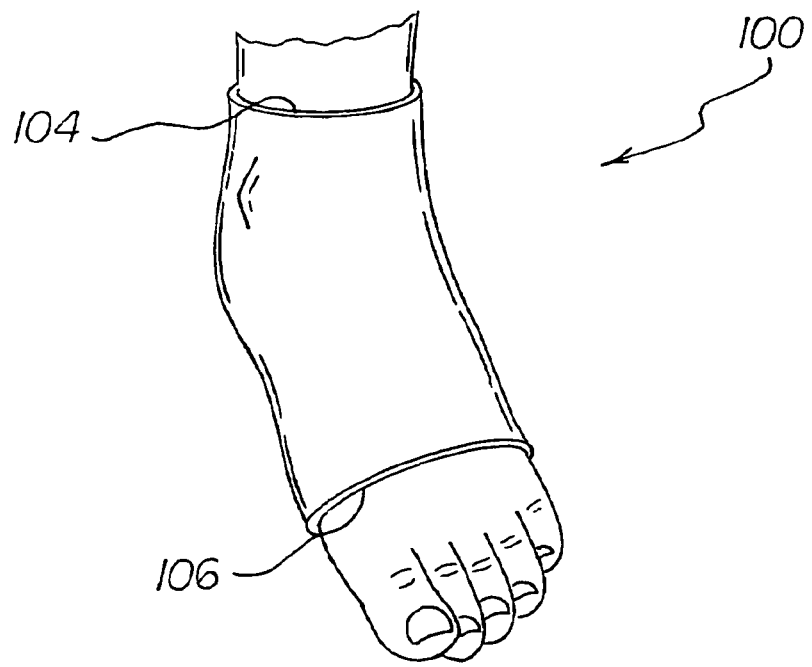
FIGS. 6 and 7 are perspective illustrations of an alternate embodiment of the invention.
Figure 7:
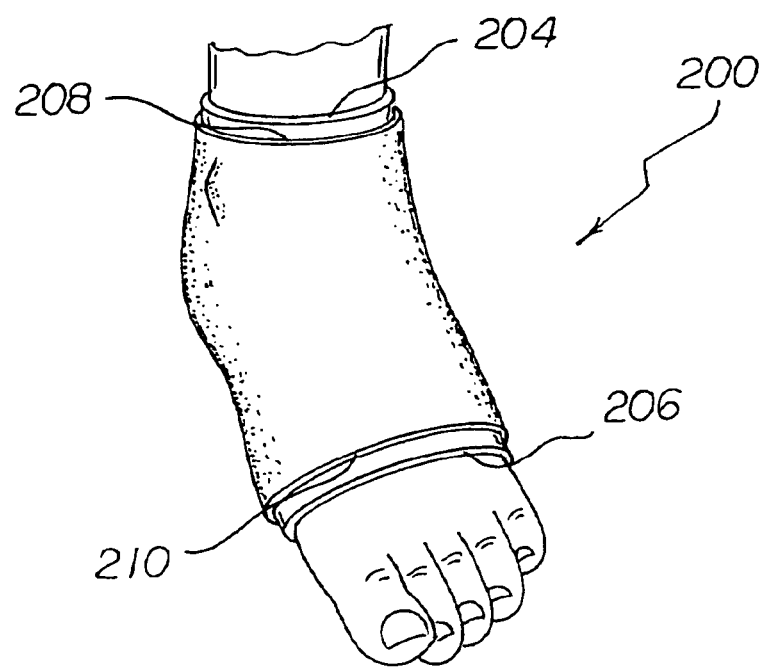

FIGS. 6 and 7 illustrate an alternate embodiment of the invention. In FIG. 6 there is shown a system 100 which includes a toe-less interior sock but no exterior sock. Such interior sock has an upper end 104 similar to the preferred embodiment described above. Such interior sock has an lower end 106 which terminates intermediate the wearer's ankle and toes. FIG. 7 shows a system 200 which includes a toe-less interior sock and a toeless exterior sock. The interior sock has an upper end 204 and a lower end 206 which terminates intermediate the wearer's ankle and toes. The exterior sock has an upper end 208 and a lower end 210 which terminates intermediate the wearer's ankle and toes. Therapeutic fluids are adapted to be provided interior of the interior sock as in the primary embodiment as described above.

The toe-less embodiment may be used with or without an exterior sock, with or without therapeutic fluids. It is ideal for spas/pedicures or for patients that have only heel involvement of their disease. In addition, the use of the interior sock alone would be ideal for preventative use when walking in public places such as the security line in airports or where multiple unseen/microscopic fungus or bacteria that are on the floors where we are made to walk. These are very contagious and spread easily. They include, for example, staph, MRSA, fungus and warts.

The present invention fills a huge avoid in foot care and protection. By locking moisture, whether using the full sock or the toe-less embodiment, the occlusion of the moisture increases the efficacy up to 50 percent. This is a wonderful product for patients that suffer from psoriasis, eczema, fungus and dermatitis of the feet.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A therapeutic sock system for increasing the effectiveness of foot medications, creams, lotions and ointments in a safe, efficient and cost effective manner comprising, in combination:

an interior sock fabricated of a flexible elastic polymer selected from the class of flexible elastic polymers including latex and vinyl, the interior sock having a cylindrical closed toe section and a cylindrical open ankle section with an intermediate heel section between the toe and ankle sections, the toe and ankle sections of the interior sock having a toe axis and an ankle axis diverging at 120 degrees from the heel section, the interior sock having a thickness of between 0.9 mils and 1.6 mils, the length of the toe section of the interior sock being 8 inches plus or minus 20 percent when measured along the toe axis, the length of the ankle portion of the interior sock being 3 inches plus or minus 20 percent when measured along the ankle axis;

an exterior sock fabricated of a ribbed knitted blend of at least 80 percent cotton and a minor portion of an elastic polymer, the exterior sock having a cylindrical closed toe section and a cylindrical open ankle section with an intermediate heel section between the toe and ankle sections, the toe and ankle sections of the exterior sock having a toe axis and an ankle axis diverging at 120 degrees from the heel section, the interior sock including textured areas around the ankle portion for increased gripping capabilities, the ankle section of the exterior sock having a common thickness throughout the majority of its extent, the length of the toe section of the exterior sock being 8 inches plus or minus 20 percent when measured along the toe axis, the length of the ankle portion of the interior sock being 2 inches plus or minus 20 percent when measured along the ankle axis; and a quantity of therapeutic fluid selected from the class of therapeutic fluids including foot medications, creams, lotions and ointments, the therapeutic fluid being located within the interior sock in contact with a foot of a user with the interior sock providing support for the therapeutic fluid and the exterior sock providing pressure and warmth to the interior sock and the therapeutic fluid.

* * * * *